United States Patent [19]
Worden et al.

[11] Patent Number: 6,054,319
[45] Date of Patent: Apr. 25, 2000

[54] METHOD AND APPARATUS FOR GROWING CELLS USING GAS OR LIQUID APHRONS

[75] Inventors: Robert Mark Worden, Holt, Mich.; Tyler T. Ames, Newark, Del.

[73] Assignee: Board of Trustees operating Michigan State University, East Lansing, Mich.

[21] Appl. No.: 09/018,327

[22] Filed: Feb. 3, 1998

[51] Int. Cl.[7] .............................. C12N 5/02; C12N 1/20; C12N 13/00

[52] U.S. Cl. .................. 435/420; 435/252.1; 435/173.1; 435/173.8; 210/695

[58] Field of Search .............................. 435/420, 252.1, 435/173.8, 173.1; 210/695

[56] References Cited

U.S. PATENT DOCUMENTS

| | | | |
|---|---|---|---|
| Re. 31,439 | 11/1983 | Rosenweig | 34/1 |
| 3,440,731 | 4/1969 | Tuthill | 34/1 |
| 3,900,420 | 8/1975 | Sebba | 252/307 |
| 4,016,293 | 4/1977 | Coughlin et al. | 426/42 |
| 4,032,407 | 6/1977 | Scott et al. | 195/127 |
| 4,115,927 | 9/1978 | Rosensweig | 34/1 |
| 4,209,591 | 6/1980 | Hendriks | 435/288 |
| 4,296,080 | 10/1981 | Rosensweig | 423/240 |
| 4,394,281 | 7/1983 | Rosensweig | 252/62.55 |
| 4,447,534 | 5/1984 | Moebus et al. | 435/161 |
| 4,655,796 | 4/1987 | Pirkle, Jr. | 55/3 |
| 4,668,379 | 5/1987 | Rosensweig et al. | 208/167 |
| 4,668,632 | 5/1987 | Young et al. | 435/284 |
| 4,746,615 | 5/1988 | Bucholz et al. | 435/311 |
| 4,931,388 | 6/1990 | Katinger | 435/41 |
| 5,009,792 | 4/1991 | Pettersen et al. | 210/705 |
| 5,010,004 | 4/1991 | Kosugi et al. | 435/134 |
| 5,073,491 | 12/1991 | Familletti | 435/240.22 |
| 5,166,072 | 11/1992 | Krauling et al. | 435/288 |
| 5,223,429 | 6/1993 | Tepic | 435/240.3 |
| 5,270,189 | 12/1993 | Scott | 435/139 |
| 5,314,644 | 5/1994 | Michelsen et al. | 261/84 |
| 5,348,871 | 9/1994 | Scott et al. | 455/165 |
| 5,409,822 | 4/1995 | Scott et al. | 435/139 |
| 5,443,985 | 8/1995 | Lu et al. | 435/240.25 |
| 5,605,673 | 2/1997 | Schutt et al. | 424/9.51 |
| 5,846,829 | 12/1998 | Worden et al. | 435/420 |

OTHER PUBLICATIONS

Seba F. Chemistry and Industry, Feb. 1985, pp. 91–92.
Chibata et al. Methods of Cell Immobilization. In: Manual of Industrial Microbiology and Biotechnology. Ed(s). Demain et al. American Society for Microbiology, 1986. Chapter 18, pp. 217–229.
Flygale et al. Enzyme Microb. Technol. (1987), 9,8, pp. 494–499. Abstract from STN BIOTECHDS Database.
Creuger, W. and A. Creuger, Biotechnology: A textbook of Industrial Microbiology, p. 1–275 (1984).
Prokop, A., R. Bajpai, and C.Ho., Recombinant DNA Technology and Applications, McGraw Hill, New York, (1991).
Vieth, W., Gene expression with plant cells. In Bioprocess engineering: Kinetics, mass transport, reactors and gene expression. John Wiley & sons: New York 265–324 (1994).
Dornenburg, H., et al., Enzyme and Microbial Technology 17:674–684 (1995).
Shuler, M., et al. Bioreactor considerations for producing flavors and pigments from plant tissue culture. In Biotechnol & food process eng; Scwartzberg, H., Rae, M., Eds Marcel Dekker: New York, pp. 45–65 (1990).
Ten Hoopen, H., et al. Possibilities, problems and pitfalls of large–scale plant cell cultures. In progress in plant cellular and molecular biology; Nijkamp, H.; Van der Plas, 1., Van Aartrijk, J., Eds: Kluwer Academic publishers: Boston. 673–681 (1990).
Sahai, O., et al., Biotechnology Progress 1:1–9 (1985).
Christou, P., Euphytia Technology 17:674–684 (1994).
Jende–Strid, B., Hereditas 119:187–204 (1993).
Yun, D., Proc. Natl. Acad. Sci USA 89:11799–11803 (1992).
Waugh, R., et al. Plant Genetic Engineering, 1–37 (1991).
Mol, J., et al., Use of genetic engineering to improve yields in cell cultures, e.g. (anti)sense DNA technology. In progress in plant Cellular and molecular biology; Nijkamp, H.; Van der Plas, L.; van Aartrijk, J., Eds: Kluwer Academic pulbishers: Boston 712–716 (1990).
Uchimiya, H., et al., Journal of Biotechnology 12:1–20 (1989).
Gulik, W., Biotechnology Progress 10:335–339 (1994).
Reinhard, E., et al., Biotechnology and Bioengineering 34:502–508 (1989).
Panda, A., et al., Enzyme Microb. Technol. 11:386–397 (1989).
McKelvey, S., et al., Biotechnol. Prog. 9:317–322 (1993).
Brodelius, R., Transport and accumulation of secondary metabolites. In Progress in plant cellular and molecular biology; Nijkamp. H.; Van der Plas, L.; Van Aartrijk, J. Eds; Kluwer Academic Publishers: Boston 567–576 (1990).
Graham, T., et al., Mol. Plant–Microbe Interact, 3:157–166 (1990).
Kudou, S., et al., Agric. Biol. Chem 55:2227–2233 (1991).
Barz, W., et al., Phenolic Metabolism in Plants 139–165 (1992).
Rosensweig, R., Science 204:57–60 (1979).
Rosensweig, R., et al. AIChE Symposium series 77:8–16 (1981).
Siegell, Powder Technology 39:215–222 (1984).
Jaraiz–M., et al., AIChE 30:951–966 (1984).
Lui, Y., at al Powder Technology 64:3–41 (1991).

(List continued on next page.)

Primary Examiner—Sandra E. Saucier
Assistant Examiner—Vera Afremova
Attorney, Agent, or Firm—Ian C. McLeod

[57] ABSTRACT

A method and bioreactor (10) apparatus is described for maintaining cells in a culture medium containing gas or liquid aphrons. A preferred microbubble generator (42, 42A) of a gas which is necessary for maintaining the cells to produce plant derived chemicals is described. Bioparticles (11) containing magnetically susceptible particles are provided in a column (12) surrounded by a solenoids (13, 14, 14A) which act to hold the bioparticles in position in the column. Preferably, one of the solenoids with a magnetically susceptible screen (24) acts as a valve to allow a portion of the bioparticles to be removed from the column.

17 Claims, 9 Drawing Sheets

OTHER PUBLICATIONS

Weng, D., et al AIChE Symposium Series on Fluidized Processes 289:107–115 (1992).

Hu, T., et al, Chem, Eng. Res. Des 65:238–242 (1987).

Bramble, J., et al Biotechnology Progress 6:452–457 (1990).

Siegell, J. Powder Technonlogy 55:127–132 (1988).

Shuler, M., Ann. N.Y. Acad. Aci 65–79 (1981).

Leckie, F., et al., Effect of bioreactor design and agitator speed on the growth and alkaloid accumulation by cultures of Catharanthus roseus 13:296–305 (1991).

Facchhini, P., et al., Biotech. Bioeng. 37:397–403 (1991).

Zhong, J., et al., Biotech, Bioeng. 38:653–658 (1991).

Dorgelo, E. et al, Chem. Eng. Sci 40:2105–2111 (1985).

Fogler, H., Elements of Chemical Reaction Engineering. Prentice–Hall: New Jersey (1986).

Bredwell et al., Applied Biotechnology 51:501–509 (1995).

Lilly, M., et al Methods in Enzymology 136:138–150 (1997).

Ames, T., and R.M. Worden, Biotechnol. Prog. 13:336–339 (1997).

Jaraiz–M., et al., Powder Technol. 38:53–61 (1984).

Yang, W., et al., Ind. Eng. Chem Process Des. Dev. 21:717–721 (1982).

Smisrod, O., et al., Tibtech 71077 (1990).

Brodelius, P., Cell Culture and Somatic Cell (Academic Press 535–547 (1984)).

Kaster, J., Michelson, D., Velander, W., Appl Biochem & Biotechnol 24/25 469–484 (1990).

Bailey, J., Ollis, D., Biochemical Engineeering Fundamentals, Second Edition, McGraw–Hill, New York (1986).

Smith, B., Roe, J., A photometric method for the determination of α–amylase in blood and urine, with use of th starch–iodine color. J. of Biol Chem 179:53 (1949).

METHOD AND APPARATUS FOR GROWING CELLS USING GAS OR LIQUID APHRONS

SUMMARY OF THE INVENTION

(1) Field of the Invention

The present invention relates to a process for growing cells, particularly to produce chemicals either intracellularly or extracellularly, in a magnetofluidized bed bioreactor apparatus using aphrons in the culture medium to provide oxygen or other necessary gases to the cells. The apparatus preferably uses a magnetic valve to allow sequential removal of a portion of bioparticles from a column after a pre-selected residence time in the bioreactor.

(2) Description of Related Art

Many secondary metabolites of living cells (procaryotes and eucaryotes) have value as pharmaceuticals, enzymatic catalysts, food colors, flavors and fragrances. This can include recombinant DNA containing cells which produce metabolites.

Plant pharmaceuticals include for instance: taxol, genistein, diadzein, codeine, morphine, quinine, shikonin, ajmalacine, and serpentine. Food product examples are anthocyanins, saffron, vanilla, and a wide variety of other fruit and vegetable flavors and texture modifying agents.

Bacteria are known to naturally produce a wide range of industrially important products. Examples include alcohols, such as ethanol; organic acids, such as lactic acid; and amino acids, such as phenylalanine (Crueger, W. And A. Crueger, Biotechnology: A text book of Industrial Microbiology 1–275 (1984)). The range of products can be widely expanded through the use of recombinant-DNA techniques. A rapidly increasing spectrum of high-value pharmaceuticals can be produced by bacteria by transferring DNA coding for those products from eucaryotic cells into bacteria (A. Prokop, R. Bajpai, and C. Ho, Recombinant DNA Technology and Applications, McGraw Hill, New York, (1991)). For instance, human insulin is now commercially produced by recombinant *E. coli* in large-scale fermentations.

Production of biochemicals from higher plants is attractive where compounds do not naturally occur in microbial or mammalian systems, or where compounds are produced by polygenic (multiple gene) processes not amenable to gene transfer (Vieth, W., Gene expression with plant cells. In Bioprocess engineering: kinetics, mass transport, reactors and gene expression. John Wiley & Sons: New York, 265–324 (1994)). The exploitation of plant production of biochemicals has been largely limited, however, to whole plant systems. While at least 30 compounds are known to accumulate in plant cell culture at concentrations equal or greater than in whole plants, literature reports of commercial production are limited to shikonin from *Lithospermum erythrorhizon* and taxol and other products from Taxus (Phyton Gesellschaft für Biotechnik mbH) (Dörnenburg, H., et al., Enzyme and Microbial Technology 17:674–684 (1995)). Plant cell culture offers several potential advantages over harvest and extraction of whole plants. Continuous production, rather than seasonal, is possible in a bioreactor where conditions can be controlled for optimal product formation. Plant cell culture can provide a high quality, uniform product while reducing labor costs (Shuler, M., et al., Bioreactor considerations for producing flavors and pigments from plant tissue culture. In Biotechnology and food process engineering; Scwartzberg, H., Rao, M., Eds; Marcel Dekker: New York, pp. 45–65 (1990)) and eliminating the effects of weather and disease.

Industrial application of plant cell culture has been limited by a number of drawbacks including slow growth rates, low product yields, intracellular storage of product, and poorly understood metabolic regulation. Perhaps the largest roadblock to industrial application of plant cell culture is low productivity per volume (Ten Hoopen, H., et al., Possibilities, problems and pitfalls of large-scale plant cell cultures. In Progress in plant cellular and molecular biology; Nijkamp, H.; Van der Plas, L.; Van Aartrijk, J. Eds; Kluwer Academic publishers: Boston, 673–681 (1990)). Production of shikonin is an example where this has been overcome however. High-yield cell lines obtained by repeated selection had a shikonin content 25 times that of the original strain (Sahai, O., et al., Biotechnology Progress 1:1–9 (1985)). In addition to isolation of high yield cell lines, genetic manipulation may enable dramatic increases in product yields. Progress in understanding of biochemical pathways and genetic engineering of plants has been reported for several systems (Dörnenburg, H., et al., Enzyme and Microbial Technology 17:674–684 (1995); Christou, P., Euphytica 74:165–185 (1994); Vieth, W., Gene expression with plant cells. In Bioprocess engineering: kinetics, mass transport, reactors and gene expression. John Wiley & Sons: New York, 265–324 (1994); Jende-Strid, B., Hereditas 119:187–204 (1993); Yun, D., Proc. Natl. Acad. Sci. USA 89:11799–11803 (1992); Waugh, R., et al., Plant Genetic Engineering, 1–37 (1991); Mol, J., et al., Use of genetic engineering to improve yields in cell cultures, e.g. (anti) sense DNA technology. In Progress in plant cellular and molecular biology; Nijkamp, H.; Van der Plas, L.; Van Aartrijk, J. Eds; Kluwer Academic publishers: Boston 712–716 (1990); Uchimiya, H., et al., Journal of Biotechnology 12:1–20 (1989)). Application of this knowledge base is likely to create new opportunities for production of plant cell biochemicals. As metabolic barriers to commercially interesting yields are overcome, other barriers to plant cell culture should simultaneously be addressed such as bioreactor design. Experiments need to be performed at an early stage in the type of reactor to be used at large scale, as growth and production rates may change completely with reactor type (Ten Hoopen, H. et al., Possibilities, problems, and pitfalls of large-scale plant cell cultures. In Progress in plant cellular and molecular biology; Nijkamp, H.; Van der Plas, L.; Van Aartrijk, J. Eds; Kluwer Academic publishers: Boston 673–681 (1990)).

Several reactor schemes are available for plant cell cultures, including stirred tanks, bubble columns, air-lift reactors, hollow-fiber membranes, liquid-dispersed trickle and incline reactors, and mist bioreactors for hairy root culture (Gulik, W., Biotechnology progress 10:335–339 (1994); Reinhard, E., et al., Biotechnology and Bioengineering 34:502–508 (1989); Panda, A., et al., Enzyme Microb. Technol. 11:386–397 (1989); McKelvey, S. et al., Biotechnol. Prog. 9:317–322 (1993)). However, each of these reactors has limitations, such as cell death from shear, insufficient mixing at high cell densities, settling of cells, and difficulty in scale-up (Panda, A., et al., Enzyme Microb. Technol. 11:386–397 (1989)). Furthermore, many of these reactors are poorly suited for a continuous operation in which the product is accumulated intracellularly.

Immobilization offers several advantages for using plant cells. Cell densities may reach 110 g/L in alginate beads, while suspension culture is limited to about 30 g/L (Sahai, O., et al., Biotechnology Progress 1:1–9 (1985)). The close proximity of immobilized cells allows intercellular communication and transport that can be important for differentiation and secondary-metabolite production (Shuler et al., 1990). Attachment and plugging caused by free cells are eliminated by immobilization (Sahai, O., Biotechnology Progress 1:1–9 (1985)).

Fluidized bed bioreactors are well suited for immobilized cell systems. Low shear forces and pressure drops prevent damage to fragile cells. Excellent contact between the gas, liquid, and solid phases eliminates the need for mechanical mixing.

An important disadvantage of conventional immobilized cell systems, however, is that plant secondary metabolites are typically stored intracellularly (Brodelius, P., Transport and accumulation of secondary metabolites. In Progress in plant cellular and molecular biology; Nijkamp, H.; Van der Plas, L.; Van Aartrijk, J. Eds; Kluwer Academic Publishers: Boston, 567–576 (1990)). Soybean isoflavonoids, as an example, exist predominantly as glucoside-malonylated conjugates (Graham, T., et al., Mol. Plant-Microbe Interact. 3:157–166 (1990); Kudou, S., et al., Agric. Biol. Chem. 55:2227–2233 (1991) which are located in the vacuole (Barz, W., et al., Phenolic Metabolism in Plants, 139–165 (1992). Permeabilization methods for release of products into the media results in low culture viability. Brodelius (Brodelius, P., In Progress in plant cellular and molecular biology, 567–576 (1990)) notes that it appears very difficult, if not impossible, to release vacuolar substances into the medium by permeabilization of the plasma membrane and the tonoplast without killing the cells.

A magnetofluidized bed (MFB) consists of a fluidized bed of magnetically susceptible particles to which a direct-current (DC) magnetic field is applied. The magnetic field induces dipoles in the particles that cause the particles to align along the field lines, thus eliminating the solids mixing that occurs in unstabilized fluidized beds. However, like conventional fluidized beds, the magnetized solids can still be passed through the bed. Continuous solids throughput without mixing (i.e. "plug flow") is possible (Rosensweig, R., Science 204:57–60 (1979); Rosensweig, R., et al., AIChE Symposium Series 77:8 (1981); Siegell, Powder Technology 39:215–222 (1984), Jaraiz-M., et al. AiChE 30:951–966 (1984); Siegell, J., Powder Technology 55:127–132 (1988)). Applications for MFBs have been reviewed by Liu, Y., et al., Powder Technology 64:3–41 (1991)) including bioreactors for continuous ethanol fermentation (Weng, D., et al., AIChE Symposium Series on Fluidized Processes 289:107–115 (1992)) and phenol degradation (Hu, T., et al., Chem. Eng. Res. Des. 65:238–242 (1987)). Bramble et al. (Bramble, J., et al., Biotechnology Progress 6:452–457 (1990)) operated a magnetofluidized bed in batch mode with plant cells (*Coffea arabica*). However, none of these bioreactors were operated in a solids-throughput mode.

The primary advantage of the MFB bioreactor is that it allows continuous processing of the bioparticles with tight control of their residence time in the reactor. A maximum in product concentration with respect to time has been observed for a variety of plant systems, including *Glycine max* (Shuler, M., Ann. N.Y. Acad. Sci. 65–79 (1981)), *Catharanthus roseus* (Leckie, F., et al., Effect of bioreactor design and agitator speed on the growth and alkaloid accumulation by cultures of *Catharanthus roseus* 13:296–305 (1991)), *Thalictrum rugosum* (Facchini, P., et al., Biotech. Bioeng. 37:397–403 (1991)), and *Perilla frutescens* (Zhong, J., et al., Biotech. Bioeng. 38:653–658 (1991)). In a MFB, the optimal residence time for product concentration can be used. In contrast, a conventional fluidized bed with a three-week average residence time, a typical axial dispersion coefficient of 4 cm$^2$/s (Dorgelo, E., et al., Chem. Eng. Sci. 40:2105–2111 (1985)), and a bioreactor length of 60 cm, has a Peclet number of $5 \times 10^{-5}$. The residence time distribution corresponding to this value is that of a stirred tank (Fogler, H., Elements of Chemical Reaction Engineering. Prentice-Hall: New Jersey (1986)), indicating that the bioparticle would be well mixed. The average product concentration would thus be lower than that of the MFB due to some product bioparticle having residence times shorter than the optimum and some longer. Additional advantages and disadvantages of MFB bioreactors have been discussed by Bramble (Bramble, J., et al. Biotechnology progress 6:452–457 (1990)).

The prior patent art in fluidized beds is demonstrated by U.S. Pat. No. 31,439 to Rosensweig; U.S. Pat. No. 3,440,731 to Tuthill; U.S. Pat. No. 4,016,293 to Coughlin et al; U.S. Pat. No. 4,032,407 to Scott et al; U.S. Pat. No. 4,115,927 to Rosensweig; U.S. Pat. No. 4,209,591 to Hendriks; U.S. Pat. No. 4,296,080 to Rosensweig; U.S. Pat. No. 4,394,281 to Rosensweig; U.S. Pat. No. 4,447,534 to Moebus et al; U.S. Pat. No. 4,655,796 to Pirkle. Jr.; U.S. Pat. No. 4,668,379 to Rosensweig et al; U.S. Pat. No. 4,746,615 to Buchholz et al; U.S. Pat. No. 4,931,388 to Katinger; U.S. Pat. No. 5,010,004 to Kosugi et al; U.S. Pat. No. 5,073,491 to Familletti; U.S. Pat. No. 5,166,072 to Krauling et al; U.S. Pat. No. 5,270,189 to Scott; U.S. Pat. No. 5,348,871 to Scott et al; and U.S. Pat. No. 5,409,822 to Scott et al.

Prior art relating to aphrons is shown by U.S. Pat. No. 3,900,420 to Sebba; U.S. Pat. No. 4,668,632 to Young et al; U.S. Pat. No. 5,009,792 to Pettersen et al; U.S. Pat. No. 5,223,429 to Tepic; U.S. Pat. No. 5,314,644 to Michelsen et al; U.S. Pat. No. 5,443,985 to Lu et al; U.S. Pat. No. 5,605,673 to Schutt et al; and Bredwell et al, Applied Biotechnology, 51:501–509 (1995). Aphrons have never been used with a magnetically stabilized bed.

There is a need for an improved magnetofluidized bed reactor apparatus and method.

OBJECTS

It is therefore an object of the present invention to provide a novel magnetofluidized bed reactor apparatus and method which uses aphrons. Another object of the invention was to provide a reactor apparatus to contact gas, liquid and solid phases with the aphrons that has the properties as follows: (a) exhibits the flow properties of a magnetically stabilized fluidized bed (MSFB); (b) allows continuous throughput of solid particles with minimal mixing of the solids; (c) exhibits rapid gas-to-liquid, or liquid-to-liquid mass-transfer rates; and (d) has a low electrical power demand to maintain magnetic stabilization. Further, it is an object of the present invention to provide a method and apparatus which is reliable and economical. These and other objects will become increasingly apparent by reference to the following description and the drawings.

DESCRIPTION OF PREFERRED EMBODIMENTS

The present invention relates to a method for maintaining cells in a culture medium and removing the cells from the culture medium, the improvement which comprises: providing a bed of bioparticles containing cells which are maintained in position by a magnetic field; circulating a culture medium containing gas or liquid aphrons through the bed of bioparticles; and removing a portion of the bioparticles from the bed.

The present invention further relates to an improved apparatus for growing cells in a culture medium and for removing the cells from the culture medium which comprises: a column with opposed ends for inlet and outlet of bioparticles containing cells, wherein the material is bound to magnetically susceptible particles to form the bioparticle; a first magnetic field generator mounted around the column between the ends which produces a magnetic field which holds the bioparticles in position in the column; a second magnetic field generator around the column between the first magnetic field generator and the outlet; magnetically susceptible screen mounted across the column which when activated acts with the second magnetic field generator to prevent the bioparticles from being removed from the column and when inactivated allows a portion of the bioparticles to pass through the screen with the first magnetic field generator activated; and a gas or liquid aphron generator for introducing the aphrons into the liquid medium.

The present invention includes both gas aphrons (which are the same as microbubbles) and liquid aphrons. The need for liquid aphrons is similar to that for using gas aphrons. In some cases, it is desirable to add a gas phase to a reactor, and in other cases, it is desirable to add an organic liquid in the aphrons. All three can be present, i.e., a bulk aqueous phase, a dispersed gas phase and a dispersed organic phase.

One common reason for adding a liquid organic phase in the aphron is to extract an inhibitory product from the aqueous phase, so that it does not build up to concentrations that retard the reaction rate. (Bryne L., et al 7:116–124 (1991)) describe the need for an organic solvent phase in biochemical reactions. A liquid organic molecule in the aphron can react with a chemical that is present in the organic phase. In other examples, there can be an inert organic carrier liquid and the reactant can be dissolved in the carrier. (Lilly, M., et al, Methods in Enzymology 136:138–150 (1997)) describe a solvent phase.

In both extraction and reaction methods, the rate of mass transfer between the aqueous and organic phases increase with the amount of interfacial area between the organic and the aqueous phases. One advantage of using liquid aphrons over conventional drops is than the aphrons have a much larger area per unit volume that the conventional drops and hence a higher mass transfer rate. A second advantage is that the liquid aphrons will disrupt the MFB to a lesser extent than the much larger, conventional drops. The same advantages apply for gas aphrons.

The present invention particularly relates to an improved method for maintaining cells in a culture medium and removing the cells from the culture medium, the improvement which comprises:

(a) providing a bed of bioparticles containing cells which are maintained in position by a magnetic field;

(b) circulating a culture medium containing microbubbles of a gas necessary for maintaining the cells through the bed of bioparticles; and (c) periodically removing a portion of the bioparticles from the bed.

Further, the present invention particularly relates to an improved apparatus for growing cells in a culture medium and for removing the cells from the culture medium which comprises:

(a) a column with opposed ends for inlet and outlet of bioparticles containing cells, wherein the material is bound to magnetically susceptible particles to form the bioparticle;

(b) a first magnetic field generator mounted around the column between the ends which produces a magnetic field which holds the bioparticles in position in the column;

(c) a second magnetic field generator around the column between the first magnetic field generator and the outlet;

(d) magnetically susceptible screen mounted across the column which when activated acts with the second magnetic field generator to prevent the bioparticles from being removed from the column and when inactivated allows a portion of the bioparticles to pass through the screen with the first magnetic field generator activated; and (e) a aphron generator for introducing a gas into the culture medium.

A fluidized bed is a collection (bed) of particles that are held suspended (fluidized) by upflowing fluid or fluids (gases and/or liquids). Fluidized beds have several useful properties; they expand and contract with changes of the fluid velocity, exhibit low pressure drop, and provide efficient heat and mass transfer between the solid and fluid phases. Furthermore, solids can be continuously transported through fluidized beds.

U.S. patent application Ser. No. 08/748,508 filed Nov. 8, 1996, with Robert M. Worden, Kenneth C. Sink, Tyler T. Ames and Vicki S. Thompson as inventors, describes a magnetically stabilized fluidized bed of bio particles and thus the content of this application is incorporated by reference herein. This invention is also described by Ames, T. and R. M. Worden, Biotechnol. Prog 13:336–339 (1997). This prior invention did not recognize that aphrons could be used in the magnetically stabilized column of bioparticles.

Fluidized beds of magnetically susceptible particles can be magnetized by the application of a magnetic field. Magnetic moments induced in the particles oppose movement of particles relative to one another. If the moments are strong enough, particle mixing is eliminated. The properties of magnetized fluidized beds are affected by the strength of the induced magnetic field (that opposes particle movement) as well as disruptive hydrodynamic forces (e.g., those arising from turbulence) that cause particle movement. When the disruptive forces are relatively weak, the bed can be magnetically stabilized. A magnetically stabilized bed has no particle mixing but still retains the key features of the fluidized bed (e.g., expands and contracts with changes in the fluid velocity). However, when the disruptive forces are relatively strong, particle mixing can only be achieved by magnetic fields high enough to produce a frozen bed. A frozen bed is characterized by a large degree of particle clumping due to strong interparticle magnetic forces. The frozen bed loses key properties of fluidized beds (e.g., the ability to expand and contract with changes in the fluid flow rate).

The types of cells which can be grown in the reactor of the present invention are numerous. Included in the definition of "cells" are procaryotic and eukaryotic animal cells and plant cells which have a rigid supporting cell structure. The products which can be recovered from the cells are as varied as the cells. The cells have to be able to be grown in a culture medium.

The "culture medium" is as varied as the cells. Typically the culture medium includes carbon and nitrogen sources, trace nutrients, salts, and hormones.

Gels, such as alginate and carrageenan and agar are preferred to bind the magnetically susceptible particles to the cells. Other binders such as adhesives and the like can be used.

The magnetically susceptible particles are preferably stainless steel. Other particles are for instance, iron and magnetite. The amount used is preferably between 1 and 50 percent by weight.

Continuous bioparticle throughput eliminates the need for metabolite release. Fresh cells can be continually added at the reactor, maintained in the reactor for the optimal length of time, and then removed for product recovery. The solids residence time is chosen to optimize the intracellular product concentration, and controlled by the rate of solids throughput. Continuous operation also minimizes bioreactor down time, and thus offers increased productivity over batch operation.

The aphrons, (gas or liquid aphrons) are defined here as small bubbles or liquid droplets that are coated with surface-active molecules (e.g., surfactants) to serve to reduce aphron coalescence and stabilize the aphrons. Aphrons vary in size, but are typically between 10 and 200 µm in diameter.

Gas aphrons provide a preferred embodiment of the present invention. Conventional gas bubbles generally are greater than 1 mm in diameter. The velocity with which a gas bubble rises through a liquid increases with the gas bubble diameter. As a result, the amount of turbulence created by a rising gas bubble also increases with the gas bubble diameter. The rise in velocity and resulting turbulence of aphrons is negligible for most three-phase fluidized-bed applications, whereas the rise velocity and turbulence associated with conventional gas bubbles is known to strongly influence three-phase fluidized bed behavior.

The advantages of aphrons in a fluidized bed reactor are as follows:

(a) Aphrons provide the gas phase with minimal disruption of the magnetized bed. By contrast, conventional bubbles generate disruptive hydrodynamic forces as they rise through the bed.

(b) As a consequence of item (a), less power is required to prevent solids mixing in magnetized fluidized beds when aphrons are used than when conventional bubbles are used. Lower power requirements translate into reduced operating costs.

(c) As a consequence of item (b), hydrodynamic properties typical of magnetically stabilized beds (e.g., the ability to expand and contract with changes in the fluid flow rate) can be retained in three phase systems using aphrons. The greater field strength needed to prevent solids mixing using conventional bubbles usually leads to a frozen bed, which is less useful for many applications.

(d) The smaller size of aphrons results in a larger gas-liquid interfacial area, and hence more rapid gas-to-liquid or liquid-to-liquid mass transfer than for conventional bubbles.

Figure 3:
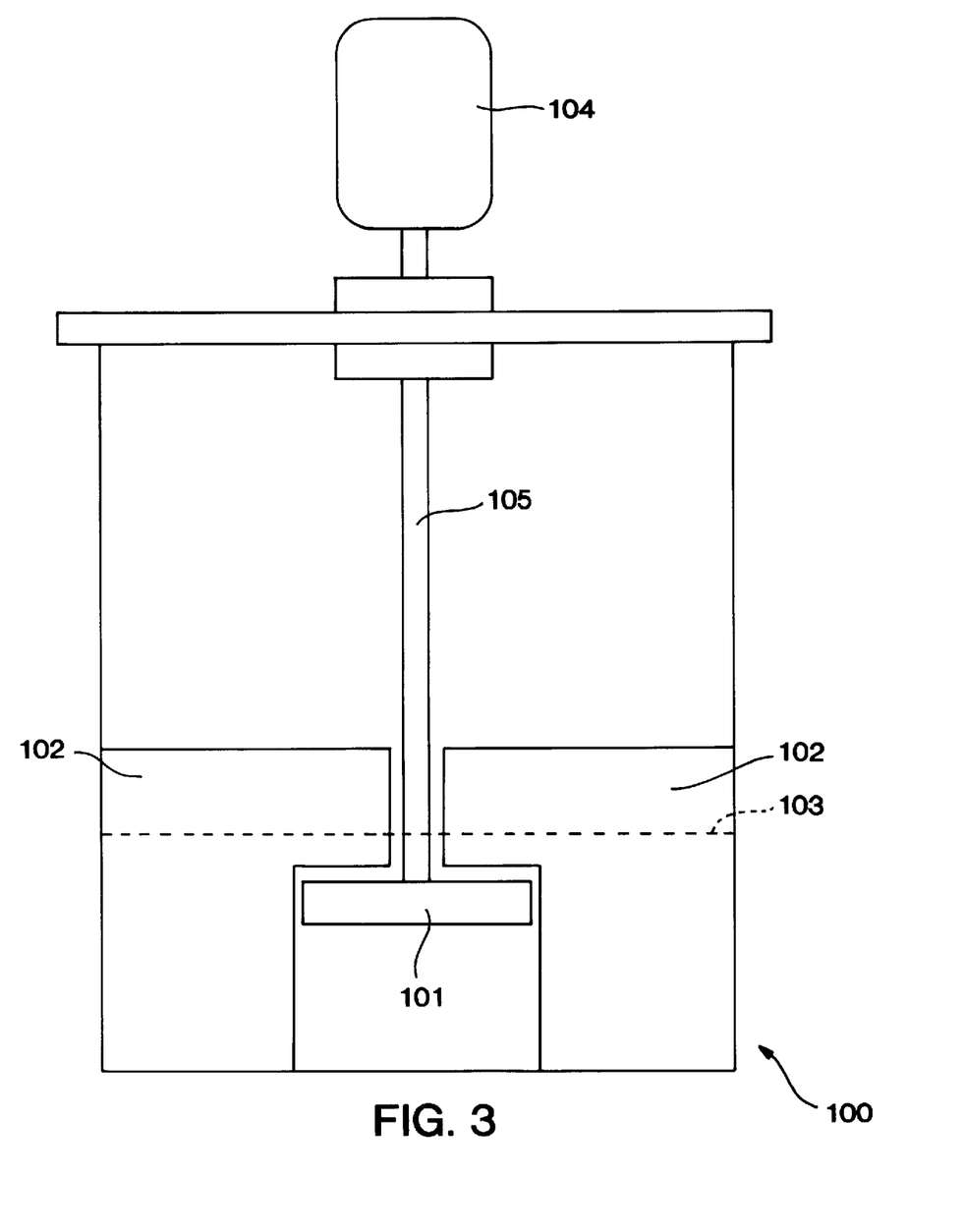
FIG. 3 is a schematic front view of a microbubble generator.

Aphrons are produced when a liquid containing a surface-active agent is placed in a high shear field in the presence of a gas phase. The generator 100 used to produce aphrons is shown in FIG. 3. A cylindrical disk 101 is rotated at several thousand rpm (up to 9,000 rmp) in the vicinity of stationary baffles 102. The resulting high shear rate between the disk 101 and baffles 102 entrains gas and breaks it up into aphrons. The initial liquid level 103 is shown. Motor 104 is used to rotate the shaft 105. However, other devices have been used to generate aphrons, including a venturi and spinning concentric cylinders (not shown).

Figure 1:
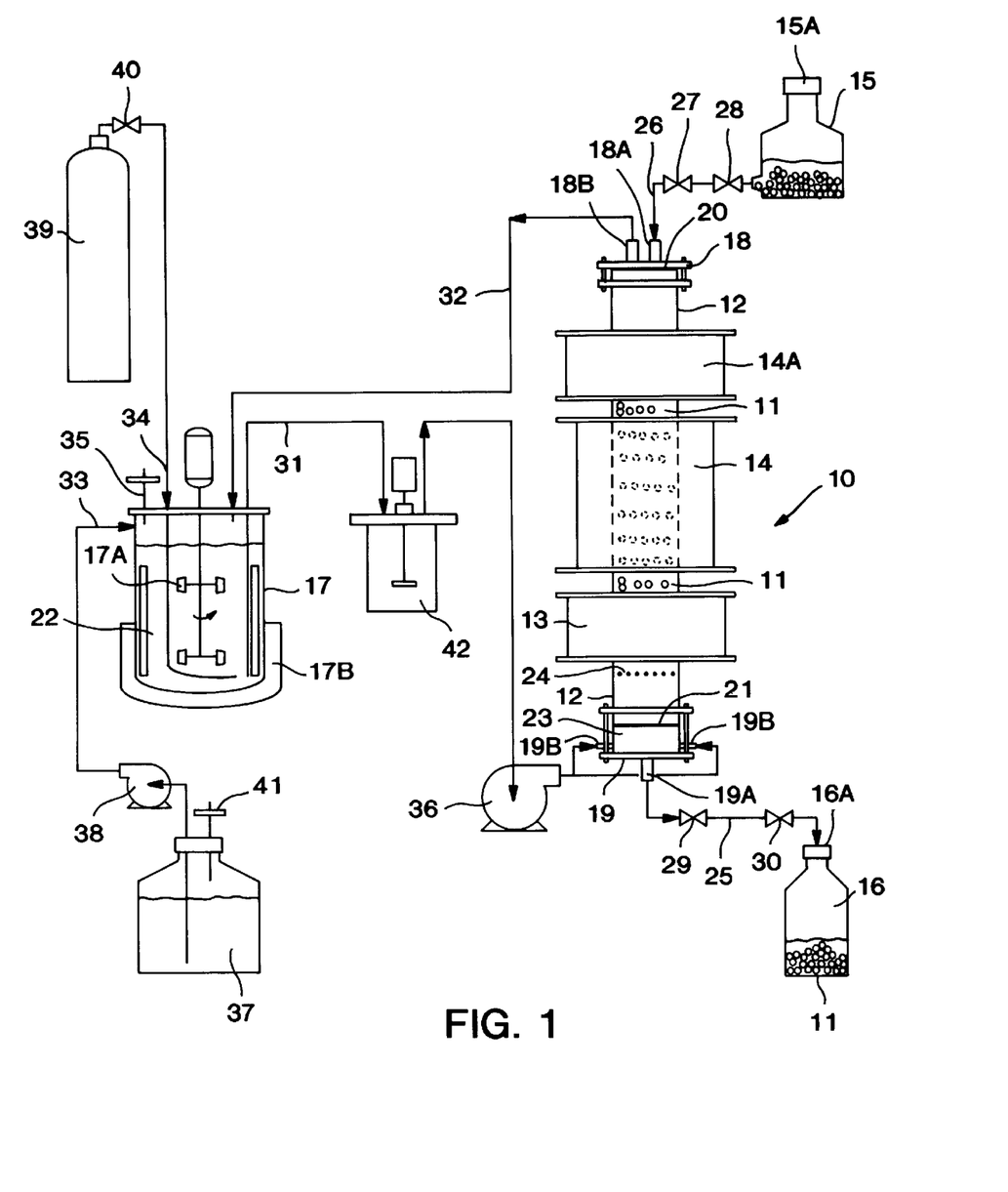
FIG. 1 is a front view of the magnetofluidized bed bioreactor 10 with a microbubble (gas aphron) generator 42.
Figure 1A:
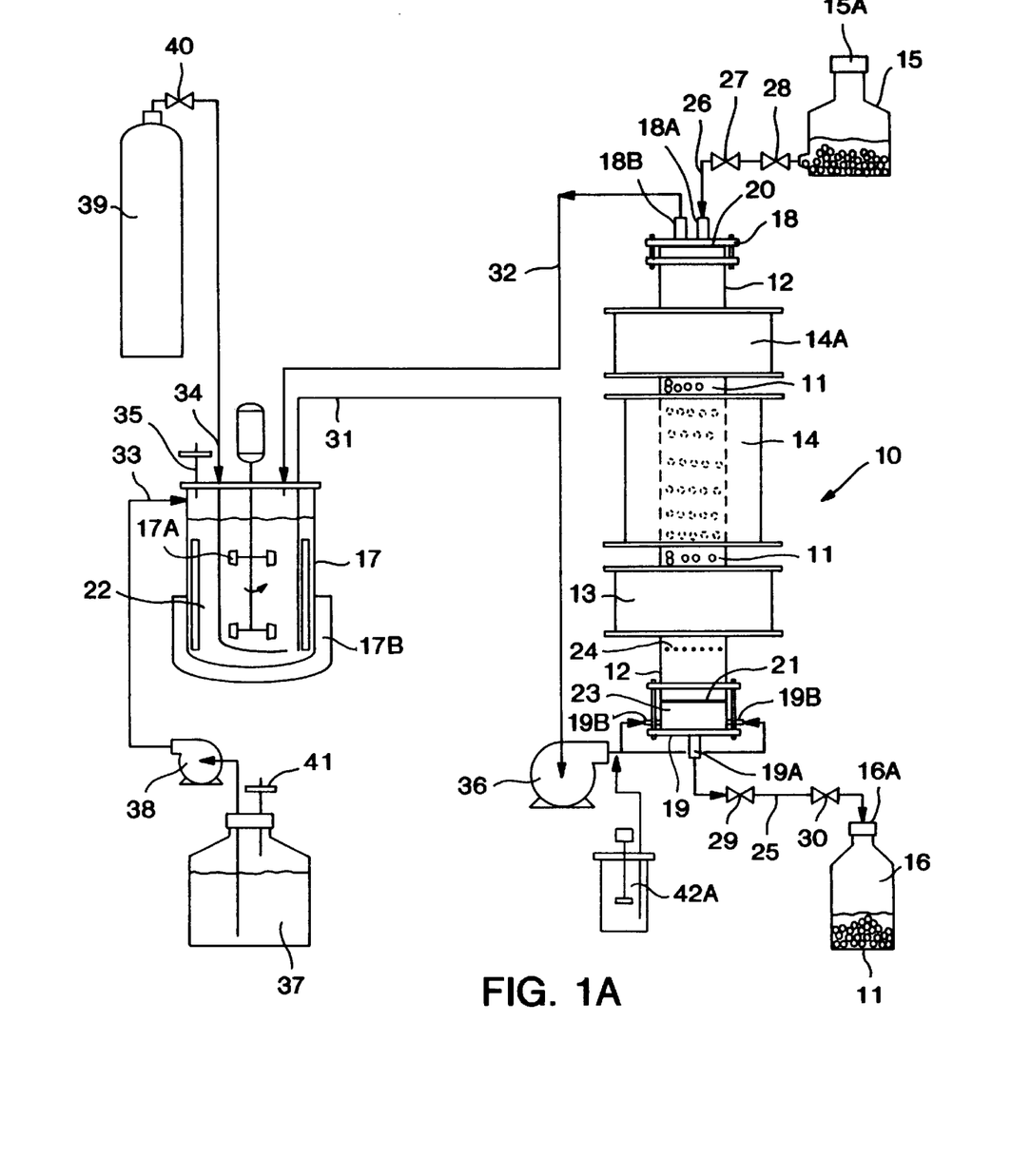
FIG. 1A shows a microbubble generator 42A in place of the generator 42 of FIG. 1.

Once formed, the aphrons must be fed, along with the liquid phase, to the column containing the magnetizable particles. The fluidized bed bioreactor 10 is shown in FIGS. 1 and 1A. In this system, the aphrons and liquid are combined at the bottom of the column 12 and flow upward through the bioparticle 11 bed. However, for particles less dense than the surrounding liquid phase, the liquid and aphrons could be fed to the top and would then flow downward in the column 12. In the preferred system, the liquid and aphrons were passed through a distribution zone consisting of a short region of the column packed with glass beads 23 before they entered the particle bed. Although this step helps mix the aphrons with the liquid phase and made the liquid flow more uniform across the column 12 cross-section, it is not essential. During operation, the particles must have magnetic moments. The use of ferromagnetic (magnetically inducible) particles is convenient, although it is possible to use particles that are permanently magnetized. In the system of the present invention, the applied magnetic field was generated by three solenoids 13, 14, 14A surrounding the column 12; however, a variety of methods can be used to generate the magnetic field. In this system, the aphrons were carried through the bioreactor by the continuous liquid phase. However, it is possible to operate the system with a continuous gas phase, whereby each aphron would be surrounded by a thin layer of liquid, like a soap bubble.

An apparatus was assembled, tested, and found to work effectively in an aqueous system. Both qualitative and quantitative observations have been made. Extensive research was conducted on three-phase magnetized fluidized beds using conventional bubbles for comparison. Less power is required to prevent liquid mixing in a system using aphrons than conventional bubbles. Significantly less power was required to prevent mixing for aphrons than conventional bubbles. In fact, the power required using aphrons appeared to be less than or equal to that needed to stabilize the bioparticles bed in the absence of any gas.

Example 1

As shown in FIGS. 1, 1A, 1B, 1C and 1D, the magnetofluidized bed bioreactor 10 is provided. The bioreactor 10, which offers continuous, plug-flow bioparticle 11 throughput, is well suited for production of intracellularly stored cell metabolites. Cell cultures are co-immobilized with ferritic stainless steel in calcium alginate spheres. Transport of bioparticle 11 through a column 12 is controlled with a magnetic valve solenoid 13. Bioparticle microscopy and Thiele modulus calculations suggested that oxygen diffusion in the bioparticle was not rate limiting. Ampicillin, Timentin, and Benlate were found to have limited phytotoxicity at concentrations useful in preventing contamination in long-term, continuous bioreactor 10 operation.

The goal was to achieve continuous production of cell secondary metabolites in the bioreactor 10 with continuous bioparticle 11 throughput. Supporting research included batch shake flask experiments to study the effect of immobilization on growth, and to determine suitable concentrations of antimicrobial agents with aphrons.

Materials and Methods

As illustrated in FIGS. 1, 1A, 1B, 1C and 1D, the main components of the MFB bioreactor 10 are the fluidized bed of the bioparticle 11, solenoids 13 and 14 and 14A, bioparticle reservoirs 15 and 16, and mixing vessel 17. The column 12 was 60 cm long and 5 cm in diameter and made of Pyrex glass with grooved ends for O-rings 20 and 21. Custom machined stainless steel endplates 18 and 19 were sealed with the O-rings 20 and 21. The head endplate 18 had a port 18A for solids inlet and a port 18B for liquid outlet. The base endplate 19 had a center outlet port 19A for solids and an annular region for liquid inlet through inlet port 19B. The annular region of column 12 was fitted with glass beads 23 (Michigan Dynamics, Heathrow Fla.) which provided liquid distribution.

Figure 1B:
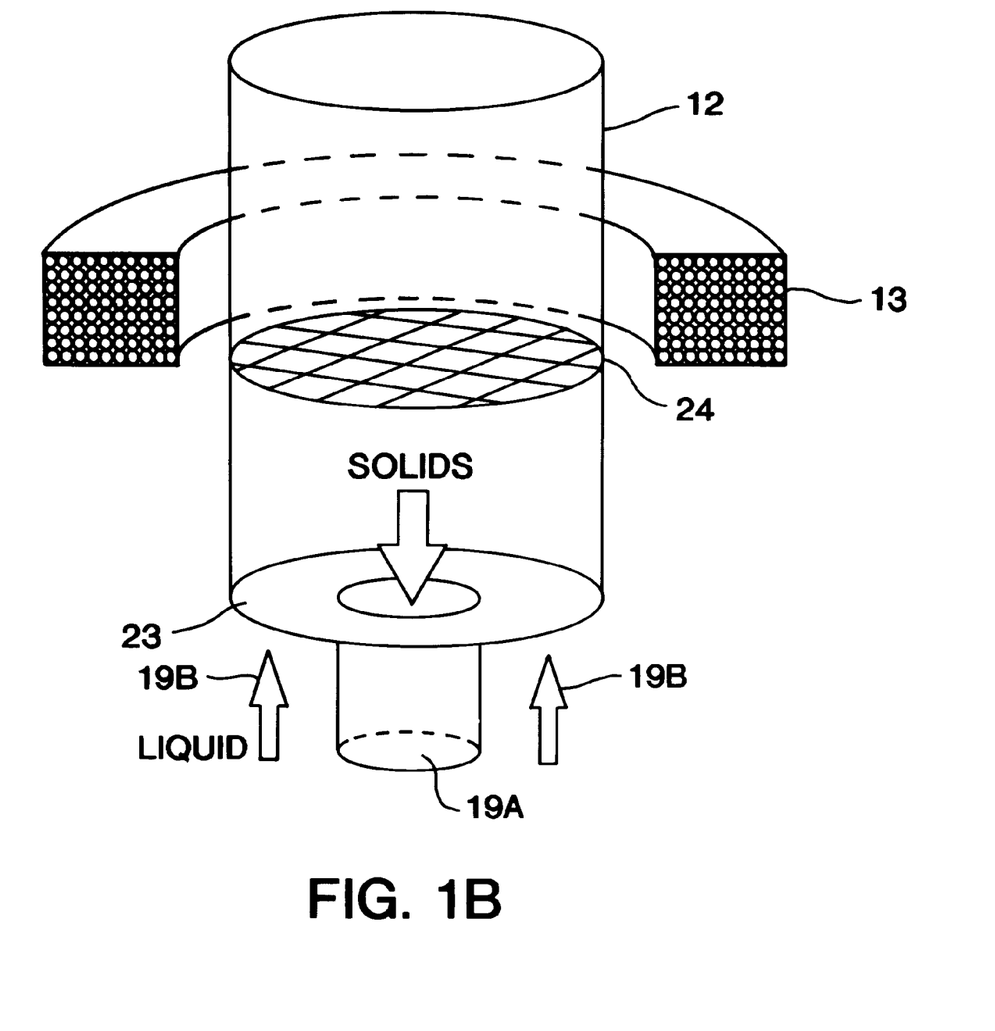
FIG. 1B is a perspective schematic partial cross-sectional view of the column 12, solenoid 13, and screen 24 forming the magnetic valve as shown in FIGS. 1 and 1A.
Figure 1C:
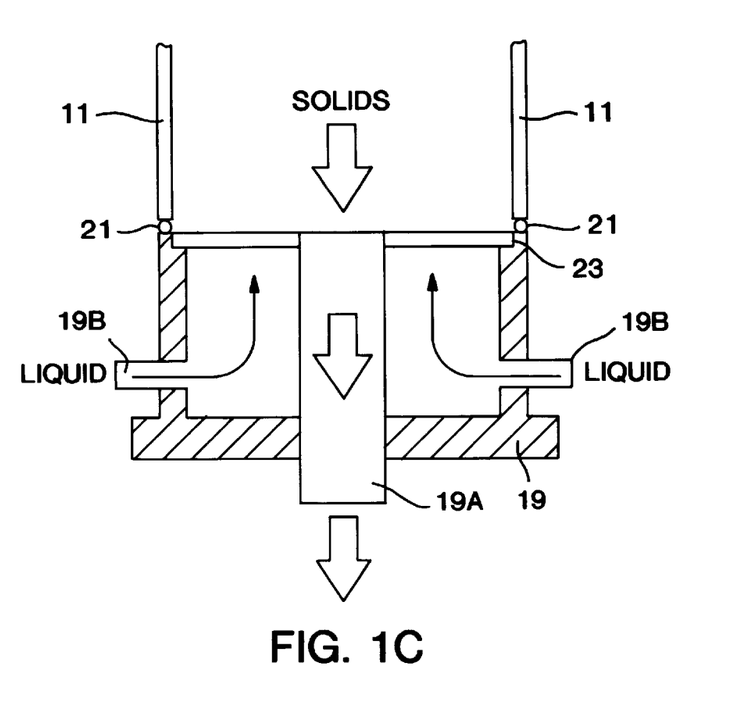
FIG. 1C is a front cross-sectional view of the base end plate 19 as shown in FIG. 1 showing the mesh 23 and o-ring 21.
Figure 1D:
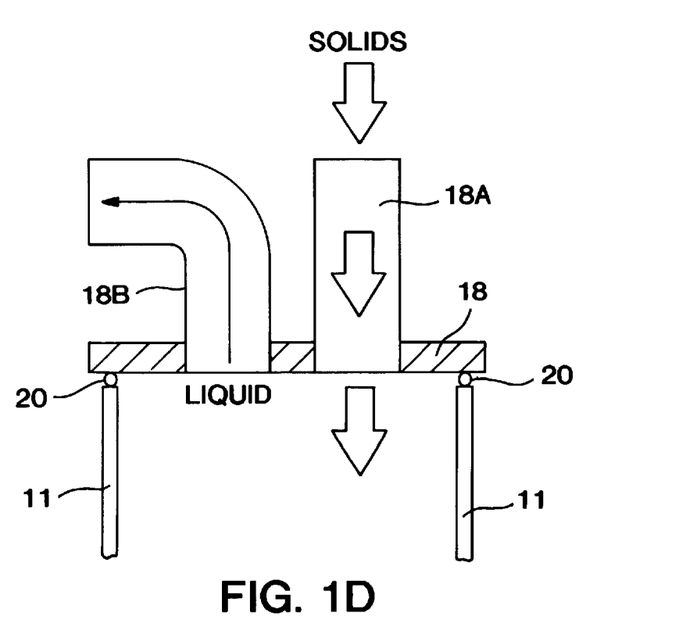
FIG. 1D is a front cross-sectional view of the head end plate 18 as shown in FIG. 1.

The solenoid 13 together with the screen 24 functioned as a magnetic valve for solids (MVS) and was used to control bioparticle flow from the MFB bioreactor 10. The MVS solenoid 13 consisted of a magnetic coil surrounding column 12 in the vicinity of a magnetically susceptible screen 24. The screen 24 openings are large enough to allow free passage of bioparticle 11 when no current is applied to the solenoid 13. Supplying power to the solenoid 14 results in an induced magnetic field at the screen 24 that stops solids flow. Details of MVS construction and operation are given by Jaraiz-M. et al. (Jaraiz-M., et al., Powder Technol. 38:53–61 (1984)) and Yang et al. (Yang, W., et al., Ind. Eng. Chem. Process Des. Dev. 21:717–721 (1982)). The magnetic valve screen 24, which consisted of a 430 stainless steel wire mesh 4×4 (Belleville Wire Cloth, Cedar Grove N.J.), was fixed to the glass with silicone sealant near the bottom of the column 12. An axial, DC magnetic field was supplied by the three solenoids 13, 14 and 14A designed to provide an approximately even field strength over the total length of the solenoids. The solenoid 13 also provided the magnetic field for the magnetic valve for solids. Power for the solenoids 13, 14 and 14A was supplied by a Kepco (Flushing, N.Y.) DC power supply (ATE 100-5M) rated at 100 volts and 5 A.

The feed bioparticle 11 reservoir 15 was a 2 L aspiration vessel sealed with a foam stopper 15A covered with aluminum foil and connected by tubing 26. A Wheaton solvent flask with a modified screw cap 16A served as the product bioparticle reservoir 16. Bioparticle outlet tubing 25 passed through the cap 16A via a hole that was sealed with silicone sealant. Both reservoirs 15 and 16 were connected to their respective headplates 18 and 19 with the tubing 25 and 26 (silicone). Clear tubing (1.5 cm ID) allowed visualization of bioparticle movement as it was controlled with pinch clamps 27, 28, 29 and 30. The mixing vessel 17 was a Bioflo II (New Brunswick, Edison N.J.) fermentation system with a 1.5 L vessel. The Bioflo II system provided agitation via stirrer 17A, temperature control via jacket 17B, and dissolved oxygen monitoring. Connections to the vessel included a suction line 31 to the base endplate 19 of the column, a return line 32 from the head endplate 18 of the column 12, a fresh medium inlet 33, a sparging gas inlet 34, and a head space vent. All tubing was norprene or silicone. Liquid was pumped to the column 12 with a high capacity Masterflex peristaltic pump 36 (Cole Parmer, Chicago). Liquid returned from the column 12 by gravity. A 20 L reservoir 37 provided fresh medium via a peristaltic pump 38 (Cole Parmer) as needed and was provided with a vent 41. An oxygen cylinder 39 regulated at 5 psi was connected through a aphron generator 42 or 42A to the vessel sparge inlet 34. The gas flow rate was controlled by a peristaltic pump 40 (Cole Parmer). The aphron generator 42 or 42A provided the aphrons for introduction into the column 12.

Gas Chromatography. Gas chromatography of the MFB gas phase was performed on a Perkin Elmer (Norwalk Conn.) Autosystem Gas Chromatograph with a thermal conductivity detector. Fixed gases were separated on a 9.1 m by 2.2 mm Hayesep DB 100/120 SS column (Alltech) with helium as the mobile phase. A Perkin Elmer 600 Series Link and PC were used for data acquisition and instrument control.

Respiration. Dissolved oxygen is measured with an Ingold $O_2$ sensor (12 mm diameter) and an Ingold Model 170 oxygen amplifier (Mettler-Toledo, Wilmington Mass.). Data is acquired with a PC, DT2801 analog and digital I/O board (Data Translation, Marlboro Mass.), and Labtech Notebook software (Laboratory Technologies, Wilmington Mass.). For suspension culture, the oxygen sensor was inserted into a 100 mL graduated cylinder via a rubber stopper. A miniature packed bed system is assembled using a 15 cm by 2.5 cm ID Pyrex column. Column ends are plugged by rubber stoppers which were connected via Tygon tubing (Cole Parmer). The bottom stopper is fitted with a metal screen to prevent passage of bioparticle. The oxygen sensor enters the column through the top stopper. Liquid was circulated with a Masterflex peristaltic pump (Cole Parmer).

Figure 2:
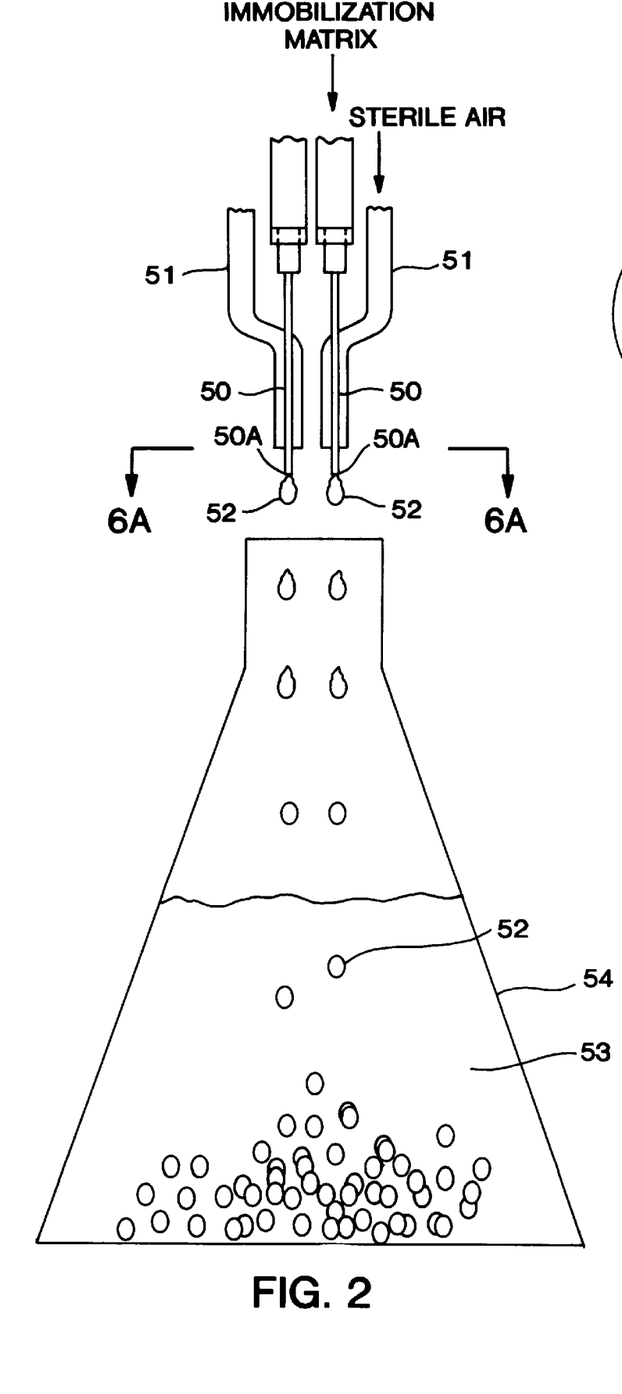
FIG. 2 is a schematic front cross-sectional view of the preferred apparatus for making the bioparticles.
Figure 2A:
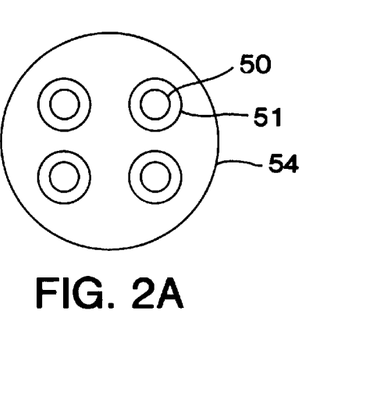
FIG. 2A is a cross-section along line A—A of FIG. 2.

Immobilization. Immobilization solution (150 mL aliquots) consisting of 2% medium viscosity sodium alginate and 25% (w/w) stainless steel particles was prepared and autoclaved in 500 mL Erlenmeyer flasks. A soybean inoculum is prepared by passing a culture through a 1 mm sieve. The filtrate is added to the immobilization solution and peristaltically pumped through a sterile bead-making apparatus into hardening solution. As shown in FIGS. 2 and 2A, the bead-making apparatus consists of feed tubing leading to four 16 gauge syringe needles 50 with flattened tips 50A. Each needle 50 is fitted with concentric tubing 51 to provide a shearing stream of sterile filtered air A that decreases bead 52 size. Beads 52 were approximately 2 mm in diameter. Hardening solution 53 (400 mL) in container 54 consists of 0.1 M calcium chloride and 20 g/L sucrose. After 20 minutes, the hardening solution is decanted and replaced with 200 mL of 1-B5 medium. For MFB use, antibiotics/antimycotics is added (50 mg/L ampicillin, 100 mg/L Timentin, and 25 mg/L Benlate). Before addition to the MFB bioreactor 10, each batch of fresh bioparticle 11 is sampled (approximately 10 mL) with a sterile 25 mL wide-mouth pipette for dry weight analysis. The entire process is conducted in a laminar flow hood. See Smidsrod, O., et al., Tibtech 71–77 (1990) and Brodelius, P., Cell Culture and Somatic Cell (Academic Press 535–547 (1984)) for further information on forming the bioparticle 11.

Cell Recovery. Bioparticle 11 volume is measured by volume displacement in a 50 mL graduated cylinder. Sample volumes are approximately 10 and 20 mL for feed and product samples respectively. Samples are placed in 125 mL Erlenmeyer flasks with approximately 50 mL of 0.2 M sodium citrate to dissolve the alginate matrix. Flasks are placed on a rotary shaker for 30 minutes at 300 rpm. Suspended cell mass is decanted while stainless steel was retained by placing a magnet on the bottom of the flask. Complete recovery of cell mass is achieved by removing the magnet, adding deionized water to wash the stainless steel, and decanting suspended cell mass with the magnet on the bottom of the flask.

Analytical Procedures. Dry Weight. Decanted cell mass is collected by filtering through dried and tared Whatmann 41 ashless filter paper using a glass microanalysis filter holder (Fisher, Pittsburgh Pa.). Samples are dried overnight at 70° C. and weighed. Samples immobilized with stainless steel are then ashed in tared, ceramic crucibles over a Bunsen burner, cooled in a desiccator, and weighed. The ash in the crucible is taken as the mass of residual stainless steel which is not separated from the soybean tissue.

Bioparticle Microscopy. Product bioparticle was sliced to obtain a cross-section from the center of the particle. The cross-sections were examined at 40 times magnification for distribution of cell mass. Both transmission and dark-field illumination are utilized. Images were acquired by mounting a CCD camera on the microscope.

Respiration. For suspension culture, the entire contents of a 250 mL shake-flask culture is put into the graduated cylinder along with fresh medium to approximately 100 mL total volume. The liquid is then sparged with air for 5 minutes. The oxygen sensor was inserted with care to remove any head space, and the stirring speed was set to give complete mixing in the cylinder. Dissolved oxygen concentration data is collected until a steady value was reached.

For immobilized culture, the apparatus described above is filled with product bioparticle. The oxygen sensor was inserted, and the remaining volume is filled with deionized water. The pump speed was set to keep the liquid well mixed.

Batch Shake Flask Cultures. Shake flask cultures as were conducted to study the effects of immobilization on *E. Coli*. The study compared suspension culture, cells immobilized in alginate, and cells immobilized in alginate with 25% (w/w) stainless steel. Replicate cultures in 1 L Erlenmeyer flasks contained 400 mL of 1-B5 medium. Suspension cultures had 30 mL of inoculum while immobilized cultures had 20 mL of inoculum in approximately 200 mL of beads. A common inoculum was used for all flasks. Immobilization followed the procedure described above. Cultures were maintained on an orbital shaker at 125 rpm.

MFB Bioreactor 10 Operation. Start-up. As the entire bioreactor 10 system is designed to fit into an autoclave, system connections made after autoclaving is minimized. Only the two connections to the column head endplate 18 are made post-autoclaving as necessitated by mounting of the solenoids 13, 14 and 14A. The fresh medium reservoir 37 is also filled prior to autoclaving and does not contain antibiotics/antimycotics. After mounting and final connections are made, the column 12 is filled with the medium 22 from reservoir 17 and liquid circulation started. The solenoids 13, 14 and 14A power supply is set at 2 A, yielding a magnetic field strength of 150–180 gauss depending on position in the column 12. The column 12 is loaded with immobilized *E. coli* bioparticle 11 (feed bioparticle) in four aliquots over the first three days of operation. Agitation in the Bioflo reservoir 17 is set at 250 rpm. Sparging with air from oxygen cylinder 39 is not started until the dissolved oxygen concentration dropped below 80% of the initial value.

Continuous Bioparticle Processing. At intervals varying from one to several days, product bioparticle 11 is removed from the bottom at outlet 19A of endplate 19 of the column 12, and feed bioparticle 11 was added to the top at the inlet 18A through endplate 18. The power supply to the solenoids 13, 14 and 14A was increased to 3 A. The upper clamp 29 of two pinch clamps 29 and 30 on the outlet tubing 25 is opened slightly to allow the length of tubing 25A between the upper and lower pinch clamps to fill with medium 22 from the column 12. At the same time, air is displaced into the column 12. Once the tubing is filled with liquid, the upper clamp 29 is completely removed. The power supply to the solenoids 13, 14 and 14A is then reduced to 0.6 A, yielding a magnetic field strength of 40 gauss at the magnetic valve 24. Bioparticle 11 is induced to fall through the screen 24 by squeezing the outlet tubing 25. No mixing in the remaining bioparticle 11 bed is likely to be observed due to the stabilization afforded by the 50–60 gauss magnetic field in the column. After the desired quantity of bioparticle 11 has passed through the screen 24, the solenoid power is returned to 3 A. While the greater portion of the released bioparticle 11 fell through the outlet hole 19A in the base endplate 19, the remainder which came to rest on the fluidization mesh 23 is removed by briefly increasing the liquid flow rate to 3 L/min. Once all the bioparticle 11 is in the outlet tubing 25, the liquid flow rate is returned to 1.6 L/min. The bottom clamp 30 is then removed, releasing the bioparticle 11 into the product reservoir 16. The bottom clamp 30 is replaced, and the process repeated once more, resulting in 150–200 mL of bioparticle in the reservoir. Following bioparticle 11 removal, additional medium is drained into the product reservoir 16 making room for addition of fresh medium 22. The solenoid power is returned to 2.0 A. The final step in removal is an aseptic exchange of the full bioparticle reservoir 16 with an empty one.

After product bioparticle 11 is removed, feed bioparticle 11 was added using a similar pinch-clamp 27 and 28 technique. Freshly prepared bioparticle 11 and medium 37 are added to the feed bioparticle reservoir. The upper of two pinch clamps 27 and 28 are removed allowing fresh liquid medium 22 and bioparticle 11 to fill the inlet tubing. Repeated squeezing of the tubing 26 facilitates movement of bioparticles 11 from the reservoir 15 to the tubing 26, displacing the liquid. Once the tubing 26 was full of bioparticle 11, the top pinch clamp 28 is replaced and the bottom pinch clamp 27 is removed allowing the bioparticle to enter the column through the head endplate 18. The bottom clamp 27 is replaced and the process repeated until all bioparticle 11 was removed from the reservoir (4–5 times). Fresh medium is then added (approximately 200 mL) by releasing the pinch clamps 27 and 28. The pinch clamps 27 and 28 were then replaced, completing the removal/addition process.

Aseptic conditions during continuous operation is verified by periodically inoculating a rich medium 22 (LB broth) with medium from the product reservoir 16. Both LB agar in petri dishes and LB medium in 125 mL Erlenmeyer shake flask cultures is employed. Shake flasks are incubated at room temperature while petri dishes are incubated at both room temperature and 30° C. for a minimum of two weeks.

Asepsis Testing. Trial runs of the bioreactor 10 is conducted to verify aseptic operation. Initially, the column 12 and endplates 18 and 19 were partially filled with LB medium, sealed, and autoclaved. The complete bioreactor 10 is then tested including liquid circulation and air sparging using LB medium. Asepsis is verified by plating of medium on LB agar after 4 and 6 days of operation. A final trial run is made to verify that bioparticle 11 could be added and removed from the bioreactor 10 aseptically. Alginate beads containing 25% stainless steel is added/removed four times over 24 days without contamination as verified by LB plating of the medium. No antimicrobial agents is used in asepsis testing.

Following start-up is a period of irregular bioparticle addition/removal. During this time, residence times are increased, and additional monitoring methods are developed.

Liquid medium 22 is added/removed along with bioparticle 11 addition/removal. For tighter control of net liquid medium 22 flow, fresh medium reservoir 37 can be continually added to the mixing vessel 17, and removed via gravity through an overflow port (not shown). Improved solids metering during addition and removal can be achieved by use of graduated tubing for bioparticle volume measurements. Evacuation of air from the bioparticle 11 outlet tubing 25 can avoid large air bubbles rising through and disrupting the bioparticles 11. Improved metering and decreased bioparticle 11 mixing can in turn lead to tighter residence time control.

Microscopy of product bioparticle 11 cross-sections supported the idea that oxygen diffusion was not rate limiting. No radical dependence of cell concentration is observed.

The bioreactor 10 has a wide variety of potential applications. The production of proteins by recombinant bacteria utilizing a plasmid vector is an example. Immobilization can enhance plasmid stability while the plug-flow biocatalyst throughput would provide removal of biocatalyst particles containing populations with a high degree of plasmid loss.

The gas phase is provided by gas aphrons. For the same volumetric flow rate of gas (in this case air), the power required to prevent mixing in a MFB is significantly less for the aphrons than for conventional bubbles. Thus, aphrons provide a savings in operational costs. Furthermore, for the same gas flow rate, experimental studies have shown that aphrons are significantly more effective in delivering oxygen to the liquid phase than sparging with conventional bubbles (Kaster, J., Michelsen, D., Velander, W., Appl. Biochem. and Biotechnol., 24/25, 469–484 (1990)). Therefore, for any system where delivery of oxygen to the liquid phase is rate limiting to process productivity, aphron aeration increases productivity while reducing operation costs. Delivery of oxygen to the liquid phase is typically rate limiting in bioreactors due to the low solubility of oxygen (Bailey, J., Ollis, D., Biochemical Engineering Fundamentals, Second Edition, McGraw-Hill, New York, (1986)).

Example 2

Figure 4:
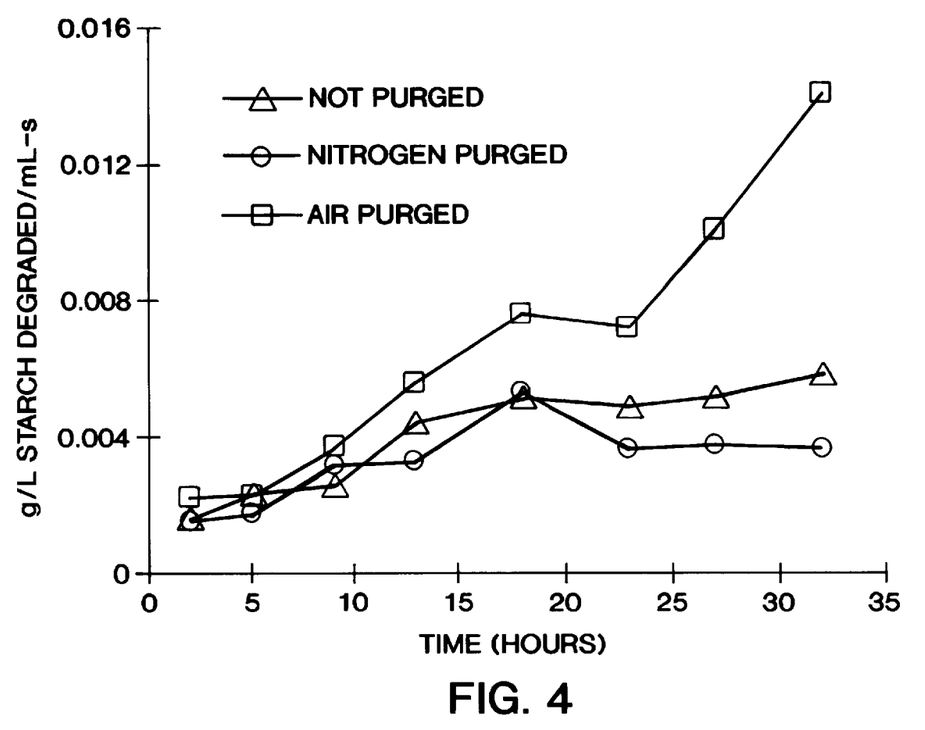
FIG. 4 is a graph showing enhancement of α-amylase production by immobilized *E. coli* due to increased dissolved oxygen levels in a preliminary batch shake flask culture.

In order to demonstrate an increase in productivity at the lab scale, a system is chosen which has relatively high oxygen demand, and the productivity is dependent on the dissolved oxygen concentration. The production of α-amylase by recombinant E. coli (strain EC 147) has been chosen as a model system. Preliminary work has established the importance of dissolved oxygen in the production of α-amylase. Batch shake flask cultures of immobilized EC 147 with aphrons have been studied with three head space composition strategies: air purged, nitrogen purged, and non-purged. The results of this study are shown in FIG. 4. The assay for α-amylase is that of Smith and Roe (Smith, B., Roe, J., A photometric method for the determination of α-amylase in blood and urine, with use of the starch-iodine color. J. Of Biol. Chem., 179, 53 (1949)).

The bioreactor 10 of FIGS. 1 or 1A is used with the aphron generator 42 or 42A. Magnetofluidized bed bioreactor experiments are conducted in the following manner, contrasting operation with aphron aeration and traditional sparging. In either case, the system is operated in batch mode with respect to the solid biocatalyst. All biocatalyst is loaded initially, and remains static in the column 12 for the duration of an experiment. Fresh media input (and corresponding overflow) is introduced by the aphrons (approximately ⅓ of the total aphron volume). Aphrons are made with media as opposed to water. For the sparged case, the volumetric air flow rate is equal to the volumetric air flow rate for aphrons (approximately ⅔ of the total volumetric rate). Fresh liquid media is added to match that which was introduced in the aphron case. The flow rate of air delivered in either case is approximately 10 mL/min.

Amylase concentrations in the media effluent are periodically determined over the course of the experiment. Dissolved oxygen and media glucose concentrations are also monitored. The effluent optical density is monitored in order to track growth of bacteria escaping the immobilization matrix. Experiments are stopped at the point where extra-biocatalyst growth becomes significant.

After an initial lag of a few to several hours, concentrations of α-amylase are expected to increase in both the sparged and aphron cases for the duration of the experiment. Concentrations in the aphron case are expected to increase at a faster rate due to the greater availability of dissolved oxygen to the E. coli. Therefore on a mass per volume per time basis, the productivity of the aphron case is greater. Furthermore, the difference in productivity is expected to increase with time due to exponential growth kinetics of E. coli.

Example 3

Figure 5:
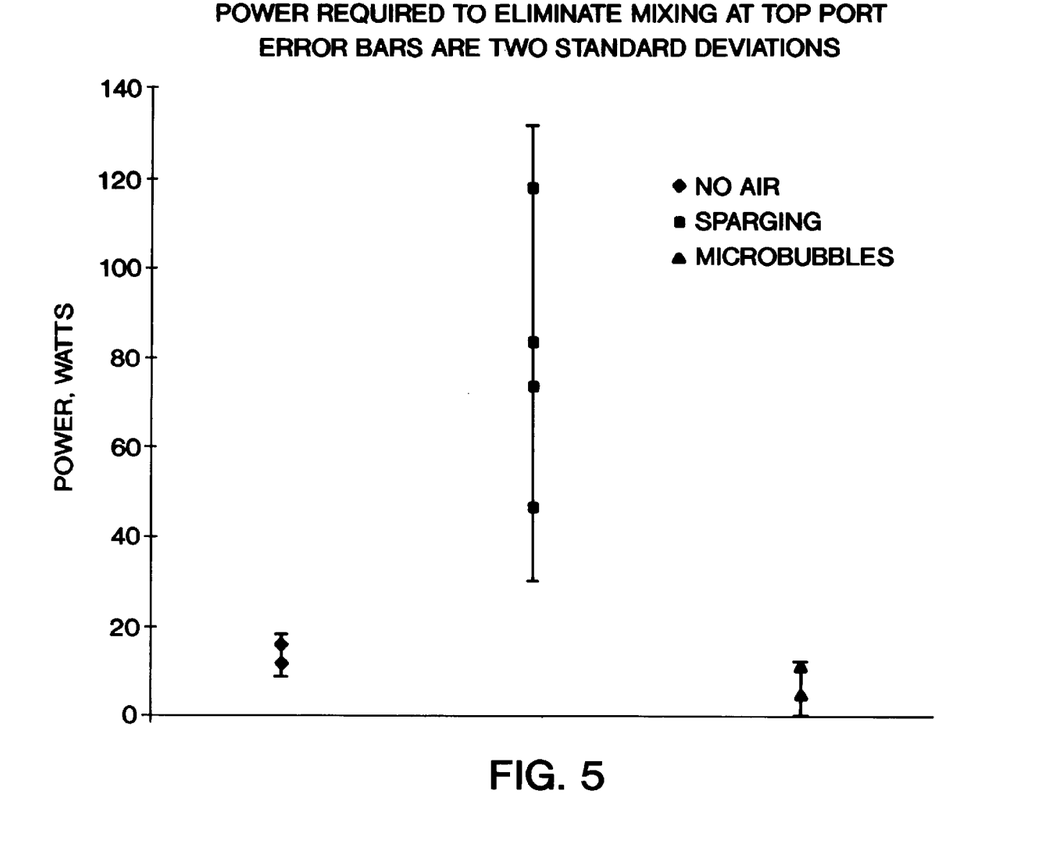
FIG. 5 is a graph showing the power required to eliminate mixing at a top port.
Figure 6:
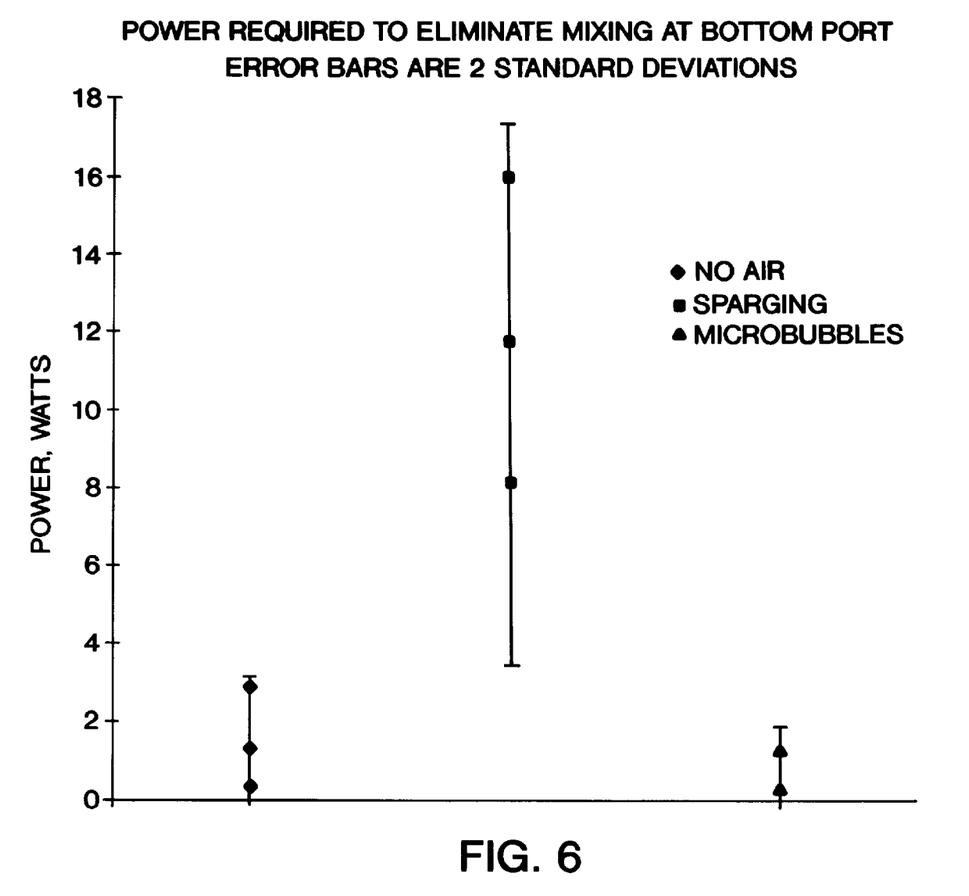
FIG. 6 is a graph showing the power required to eliminate mixing at the bottom port.

FIGS. 5 and 6 show the experimental data that indicates using aphrons reduces the electric power (supplied to the solenoid) required to prevent solids mixing relative to existing methods in a fluidized bed a reactor such as bioreactor 10. FIG. 5 shows the power requirements to prevent solids mixing at the top of the fluidized bed, and FIG. 6 shows the power requirements at the bottom of the bed. At the ends of the bed, the magnetic field is weakest, and hence particle movement would be seen at the ends before the middle.

Three cases are shown in each of FIGS. 5 and 6: no gas added, gas added in the form of gas aphrons (microbubbles), and gas added in the form of conventional bubbles. The same volumetric gas flow rate was used for the microbubbles and the conventional bubbles. The error bars indicate the 95% confidence intervals on the data. Thus, at the 95% confidence level, gas aphrons require less power for stabilization than conventional bubbles. Based on the mean values, there is a tenfold reduction of power required for microbubbles relative to conventional bubbles at the bottom of the column and an eight-fold reduction at the top port.

It is intended that the foregoing description be only illustrative of the present invention and that the present invention be limited only by the hereinafter appended claims.

We claim:

1. In a method for maintaining cells in a culture medium and removing the cells from the culture medium, the improvement which comprises:
    (a) providing a bed of magnetically susceptible bioparticles containing cells which are maintained in position in the bed by a magnetic field maintained by electrical power;
    (b) circulating a culture medium containing gas or liquid aphrons through the bed of bioparticles; and (c) removing a portion of the bioparticles from the bed, wherein the electrical power required to produce the magnetic field and maintain the bioparticles in the position in the bed with the gas aphrons is equal to or less than the power required to hold the bioparticles in position in a middle portion of the bed without the gas aphrons and less than with gas bubbles greater than 1 mm in diameter in place of the aphrons.

2. The method of claim 1 wherein the cells are bacterial or plant cells.

3. The method of claim 1 wherein the aphrons contain oxygen which is necessary for maintaining the cells.

4. The method of claim 3 wherein the source of the oxygen is air.

5. In a method for maintaining cells in a culture medium and removing the cells from the culture medium, the improvement which comprises:

(a) providing in a column a bed of magnetically susceptible bioparticles containing cells which are maintained in position by a magnetic field maintained by electrical power;

(b) circulating a culture medium containing gas aphrons through the bed of bioparticles; and (c) adding and removing a portion of the bioparticles to and from the bed, wherein the electrical power required to produce the magnetic field and maintain the bioparticles in the position in the bed with the aphrons is equal to or less than the power required to hold the bioparticles in position in a middle portion of the bed without the gas aphrons and less than with gas bubbles greater than 1 mm in diameter in place of the aphrons.

6. The method of claim 5 wherein the cells are bacterial cells.

7. The method of claim 5 wherein the aphrons contain oxygen as the gas which is necessary for maintaining the cells.

8. The method of claim 7 wherein the source of the oxygen is air.

9. The method of claim 5 wherein a gel is used to bind the particles and the cells together.

10. The method of claim 9 wherein the gel is alginate and wherein the gel upon formation contains a liquid growth media for the cells.

11. The method of claim 10 wherein the bioparticle is a bead of the gel, the cells and magnetically susceptible particles, which is formed at a tip of a needle and removed with a sterilized gas stream into a hardening solution of a salt which is non-toxic to the cells.

12. The method of claim 11 wherein the magnetically susceptible particles are stainless steel.

13. The method of claim 5 wherein the column is vertically oriented, wherein the inlet end of the column is an upper part where the bioparticles are added and wherein the outlet end of the column is a lower part where the particles are removed.

14. The method of claim 13 wherein the culture medium is circulated from the outlet of the column to the inlet end of the column for the bioparticles.

15. The method of claim 5 wherein the aphrons are formed in the culture medium which is then circulated to the column.

16. The method of claim 5 wherein the addition of the bioparticles to the column is continuous or periodic over an extended time period.

17. The method of claim 5 wherein in addition a chemical is expressed by the cells and is removed from the column with the culture medium.

* * * * *